(12) United States Patent  
Hyde et al.

(10) Patent No.: US 8,412,487 B2  
(45) Date of Patent: *Apr. 2, 2013

(54) SELF HEATING MONITOR FOR SIGE AND SOI CMOS DEVICES

(75) Inventors: Paul A. Hyde, Essex Junction, VT (US); Edward J. Nowak, Essex Junction, VT (US)

(73) Assignee: International Business Machines Corporation, Armonk, NY (US)

( * ) Notice: Subject to any disclaimer, the term of this patent is extended or adjusted under 35 U.S.C. 154(b) by 182 days.

This patent is subject to a terminal disclaimer.

(21) Appl. No.: 12/899,868

(22) Filed: Oct. 7, 2010

(65) Prior Publication Data

US 2011/0029274 A1 Feb. 3, 2011

Related U.S. Application Data

(62) Division of application No. 11/769,064, filed on Jun. 27, 2007, now Pat. No. 7,862,233, which is a division of application No. 10/711,224, filed on Sep. 2, 2004, now Pat. No. 7,406,397.

(51) Int. Cl.  
*G21C 17/112* (2006.01)

(52) U.S. Cl. ..................................... 702/182

(58) Field of Classification Search ............ 702/57, 702/119, 130, 136, 182  
See application file for complete search history.

(56) References Cited

U.S. PATENT DOCUMENTS

| | | | |
|---|---|---|---|
| 3,308,271 A | 3/1967 | Hilbiber | |
| 3,393,328 A | 7/1968 | Meadows et al. | |
| 3,667,064 A | 5/1972 | Thornton et al. | |
| 3,675,484 A | 7/1972 | Pederson | |
| 3,809,928 A | 5/1974 | Evans | |
| 3,820,236 A | 6/1974 | Haitz | |
| 3,978,418 A | 8/1976 | Louw | |
| 4,579,600 A | 4/1986 | Shah et al. | |
| 4,760,434 A | 7/1988 | Tsuzuki et al. | |
| 4,779,161 A | 10/1988 | DeShazo, Jr. | |
| 4,924,212 A | 5/1990 | Fruhauf et al. | |
| 4,955,380 A | 9/1990 | Edell | |
| 5,100,829 A | 3/1992 | Fay et al. | |
| 5,155,561 A | 10/1992 | Bozler et al. | |
| 5,265,957 A | 11/1993 | Moslehi et al. | |
| 5,302,024 A | 4/1994 | Blum | |
| 5,317,176 A | 5/1994 | Schaper et al. | |
| 5,414,370 A | 5/1995 | Hashinaga et al. | |
| 5,634,718 A | 6/1997 | Martinis et al. | |
| 6,111,280 A | 8/2000 | Gardner et al. | |
| 6,476,483 B1 | 11/2002 | Adler et al. | |
| 6,786,639 B2 | 9/2004 | Covi et al. | |
| 6,914,764 B2 | 7/2005 | Clabes et al. | |

(Continued)

FOREIGN PATENT DOCUMENTS

DE 3831012 3/1990  
JP 5235254 9/1993

(Continued)

*Primary Examiner* — Mohamed Charioui  
(74) *Attorney, Agent, or Firm* — Michael J. Le Strange; Roberts Mlotkowski Safran & Cole, P.C.

(57) ABSTRACT

A structure, apparatus and method for deterring the temperature of an active region in semiconductor, particularly a FET is provided. A pair FETs are arranged on a silicon island a prescribed distance from one another where the silicon island is surrounded by a thermal insulator. One FET is heated by a current driven therethrough. The other FET functions as a temperature sensor by having a change in an electrical characteristic versus temperature monitored. By arranging multiple pairs of FETs separated by different known distances, the temperature of the active region of one of the FETs may be determined during operation at various driving currents.

13 Claims, 12 Drawing Sheets

U.S. PATENT DOCUMENTS

| | | |
|---|---|---|
| 7,009,269 B2 | 3/2006 | Yasuda |
| 7,176,508 B2 * | 2/2007 | Joshi et al. .................... 257/253 |
| 7,357,035 B2 | 4/2008 | Liu et al. |
| 7,406,397 B2 * | 7/2008 | Hyde et al. .................... 702/182 |
| 7,723,816 B2 | 5/2010 | Bartley et al. |
| 2003/0189231 A1 | 10/2003 | Clevenger et al. |
| 2004/0075140 A1 | 4/2004 | Baltes et al. |
| 2004/0264093 A1 * | 12/2004 | Boerstler et al. .............. 361/103 |
| 2006/0197154 A1 | 9/2006 | Pelella et al. |
| 2007/0206656 A1 | 9/2007 | Franch et al. |
| 2008/0179713 A1 | 7/2008 | Landsberger et al. |
| 2009/0295457 A1 | 12/2009 | Mowry et al. |

FOREIGN PATENT DOCUMENTS

| | | |
|---|---|---|
| JP | 200115655 | 1/2001 |
| JP | 2002296121 | 10/2002 |
| RU | 2122713 | 11/1998 |

* cited by examiner

SELF HEATING MONITOR FOR SIGE AND SOI CMOS DEVICES

CROSS REFERENCE TO RELATED APPLICATIONS

This application is a divisional application of U.S. application Ser. No. 11/769,064, filed on Jun. 27, 2007, which is a divisional application of U.S. application Ser. No. 10/711,224, filed on Sep. 2, 2004, now U.S. Pat. No. 7,406,397, the contents of both applications are incorporated by reference herein in their entirety.

BACKGROUND OF THE INVENTION

1. Field of the Invention

The invention relates to semiconductor circuit design, and more particularly to modeling temperatures of a self-heating semiconductor device.

2. Background Description

Accurate measurement of self-heating of SOI and SiGe based MOSFET devices is important because DC currents of such devices are typically depressed significantly due to self-heating. This is in contrast to CMOS circuits where transients are too rapid for significant self-heating to occur. Thus, simulation (compact) models must be adjusted to correctly account for self-heating in order to correctly predict circuit performance. In SOI technologies, this effect ranges from about 3 percent to 12 percent, while in SGOI (SiGe on SOI) these effects are expected to exceed 30 percent.

Such large temperature effects in SGOI devices are due in part to the active region of the device being almost entirely surrounded by layers of material having poor thermal conductivity properties. For example, the active region of the SGOI device is SiGe, and the SiGe is arranged on top of an oxide layer. The SiGe layer has a limited length and width on top of the oxide layer, and thus forms what is referred to as a "island" on the oxide layer. During subsequent fabrication steps, the SiGe island is surrounded on its sides by an oxide, and then further covered over its top by an oxide. Thus, the SiGe island is relatively small and almost entirely surrounded by an oxide. Due to the surrounding oxide, the SiGe island has extremely limited thermal pathways by which to dissipate any heat generated in the SiGe island.

The small dimensions of the SiGe island also increase the device's susceptibility to thermal effects. In particular, because the SiGe island is relatively small, it has a comparatively low thermal mass. With the low thermal mass, the SiGe island quickly responds to any heating by a device thereon. As such, the SiGe island itself fails to act as its own heat sink for the device and the device quickly heats the island up to the devices own temperature. Thus, any device fabricated on the SiGe island will be particularly influenced by its own self-heating effects.

Known methods of measuring semiconductor device performance versus temperature include placing a diode proximate to the device for which the temperature will be measured, and using the diode's change in electrical performance as a function of temperature to measure the temperature at that point. However, such a method is difficult to implement because it is difficult to build such a diode close to a device to be measured to provide an accurate gauge of the active region of the device.

Another method of measuring the temperature effect on the electrical characteristics of a semiconductor device includes running the device at a particular power level to heat itself, and using the device's own change in electrical characteristics as a function of temperature to determine the temperature of the device. While simple to fabricate such a temperature measurement configuration, the data produced by such a configuration is less than reliable because of various hysteresis-like effects. For example, the device's sensitivity to temperature changes, may be based on, for example, among other things, on the prior electrical history of the device. Such a sensitivity to electrical history makes determining the actual temperature of the device to be less than reliable.

The invention is designed to solve one or more of the above-mentioned problems.

SUMMARY OF THE INVENTION

In a first aspect of the invention, a method of measuring performance of a device includes thermally coupling a first heating device to a first sensing device, and generating heat at the first heating device. The method also includes measuring a change in at least one electrical characteristic of the first sensing device caused by the heat generated at the first heating device, and calculating a temperature of the first heating device using the measured change in the at least one electrical characteristic.

In another aspect of the invention, a method of measuring performance of a device, includes thermally coupling a heating transistor to a measurement transistor at one or more predetermined distance, and calibrating the measurement transistor by measuring a particular electrical characteristic of an active region of the measurement transistor with the measurement transitory held at a known temperature. The method also includes generating heat at the heating transistor, and incrementally measuring a change in the at least one electrical characteristic of the measurement transistor caused by the heat generated at the heating transistor. The method additionally includes calculating a temperature of the heating transistor using the measured change in the at least one electrical characteristic.

In another aspect of the invention, an apparatus for measuring semiconductor device temperature, includes a silicon island, and at least one pair of transistors, each pair of the at least one pair of transistors comprises a transistor configured to generate heat and a transistor configured to sense temperature, wherein each transistor of each pair of transistors is arranged a prescribed distance from its corresponding transistor.

In another aspect of the invention, an apparatus for measuring semiconductor device temperature, includes at least one silicon island, and at least one heating field effect transistor configurable to generate heat arranged within the silicon island. The apparatus also includes at least one sensing field effect transistor arranged within the at least one silicon island corresponding to each heating field effect transistor of the at least one heating field effect transistor, wherein each sensing field effect transistor is arranged a prescribed distance from its corresponding heating field effect transistor and each sensing field effect transistor is configurable to sense a temperature. The apparatus additionally includes means to calculate a temperature of the each heating field effect transistor using a measured change in at least one electrical characteristic of the each sensing field effect transistor caused by the heat generated at the each heating field effect transistor.

In another aspect of the invention, an apparatus for determining the temperature of an active region of a semiconductor device includes three silicon sections, and three pairs of active regions, wherein each pair of active regions is arranged on a respective silicon section, wherein each pair of active regions is configurable to produce and sense heat. The apparatus also includes three thermal conductors, wherein each thermal conductor is arranged between each active region of each respective pair of active regions.

In another aspect of the invention, a computer program product comprising a computer usable medium having readable program code embodied in the medium, the computer program product includes at least one component to measure a change in at least one electrical characteristic of a first sensing device caused by heat generated at a first heating device, and calculate a temperature of the first heating device using the measured change in the at least one electrical characteristic.

DETAILED DESCRIPTION OF EMBODIMENTS OF THE INVENTION

The invention is directed to determining the temperature of an active region of a device fabricated using SGOI technology as a function of electrical power through the device. Such information may be used to characterize the effect of temperature on the performance characteristics of the device. This information may be utilized by design engineers to predict device performance during the circuit layout process, as a function of temperature, and to accommodate such temperature effects in the circuit design.

To reliably measure the temperature of a semiconductor device, and thereby determine the effects on performance of the device, a method includes fabricating two devices in thermal communication with one another, where the first device is run at a predetermined power level, and the second device is a prescribed distance from the first device. The second device, otherwise known as the measuring device, is capable of providing temperature information at its position as a function of the first device, e.g., power level of the heating device.

Figure 1:
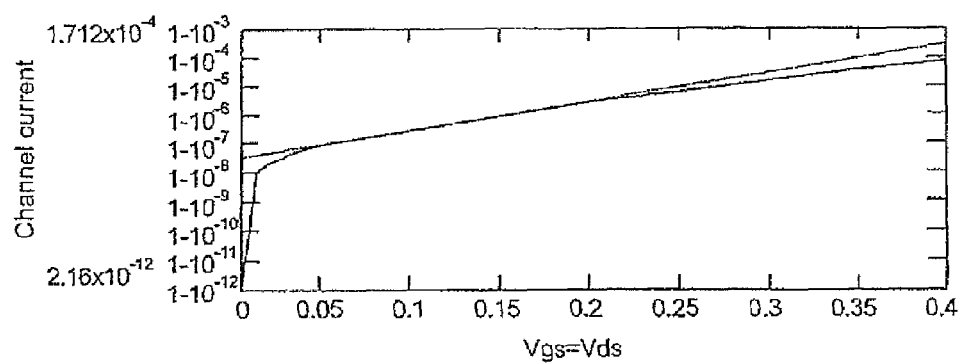
FIG. 1 is a graph of sub-threshold voltage slope versus power at an ambient temperature of 25° C.

In operation, a particular electrical characteristic of the second device is monitored to determine the temperature of the second device. This characteristic may be, for example, the sub-threshold voltage slope (also referred to as "Sub Vt") as shown in FIG. 1. In this embodiment, multiple devices are used at varying distances from the heating device to make various temperature measurements at varying distances. The measurements are used to calculate the temperature of the active region of the heating device by extrapolating the distanced-based temperature measurements back to the origin, i.e., the position of heating device.

In one embodiment, the fabricated device may include multiple SiGe islands which are fabricated where each SiGe island has its own measurement and heating device pair. For example, two FETs may be fabricated on a SiGe island a prescribed distance apart. After fabrication, a particular electrical characteristic of the second FET is measured at multiple ambient temperatures. The power levels and distances as well as other measurable phenomena and features are shown for illustration purposes in FIGS. 1 and 2 as well as the exemplary data and results shown in Tables 1-5. The method is illustrated in more detail in FIGS. 9 and 10 as discussed below.

By carrying out the measurement process for each measurement/heating device pair, the temperature and power information can be used to calculate the temperature of the active device. Although the measurement device typically has multiple electrical characteristics which will vary as a function of its temperature, an embodiment of the invention uses a sub-threshold voltage slope as a function of temperature to measure temperature.

Referring to FIG. 1, a graph showing sub-threshold voltage slope versus power at 25° C. ambient temperature is shown. The y-axis represents channel current of the measurement device, and the x-axis represents various voltages as the source input voltage is varied, where the two gates and the two drains of the devices are common to one another making Vgs (voltage between the gate and source) equal to Vds (voltage between the drain and source). Accordingly, Vgs=Vds as noted on the x-axis of FIG. 1. The common diffusion input and the measurement source may be connected with Kelvin connectors. The information of FIG. 1 is an example of an electrical characteristic of the sensing device from which its temperature is inferred. This information may be used in the method of the invention as described herein.

The data for each power point is a voltage ramp of the measurement source from, for example, $V_{gs}=V_{ds}=1.0$ V to $V_{gs}=V_{ds}=0.6$ in 0.010V increments. The sub-threshold voltage slope is fit below Vt and above the point where the behavior deviates from log-linear. For typical devices, $V_{gs}=V_{ds}=0.1$ v to 0.2 v was used. For reference, the single point Vt is 11.25 .mu.A for a device. It should be noted that similar plots are typically constructed and the slope calculated for a device at 50° C., 75° C., and 100° C. with no power in the heating device. From these plots, the relationship between sub-threshold voltage slope and temperature of the measurement device may be determined. The temperature of the measurement device can be determined by comparing the sub-threshold voltage slope at a given heating device power to the relationship features sub-threshold slope and temperature previously determined with no power to the heating device.

Figure 2:
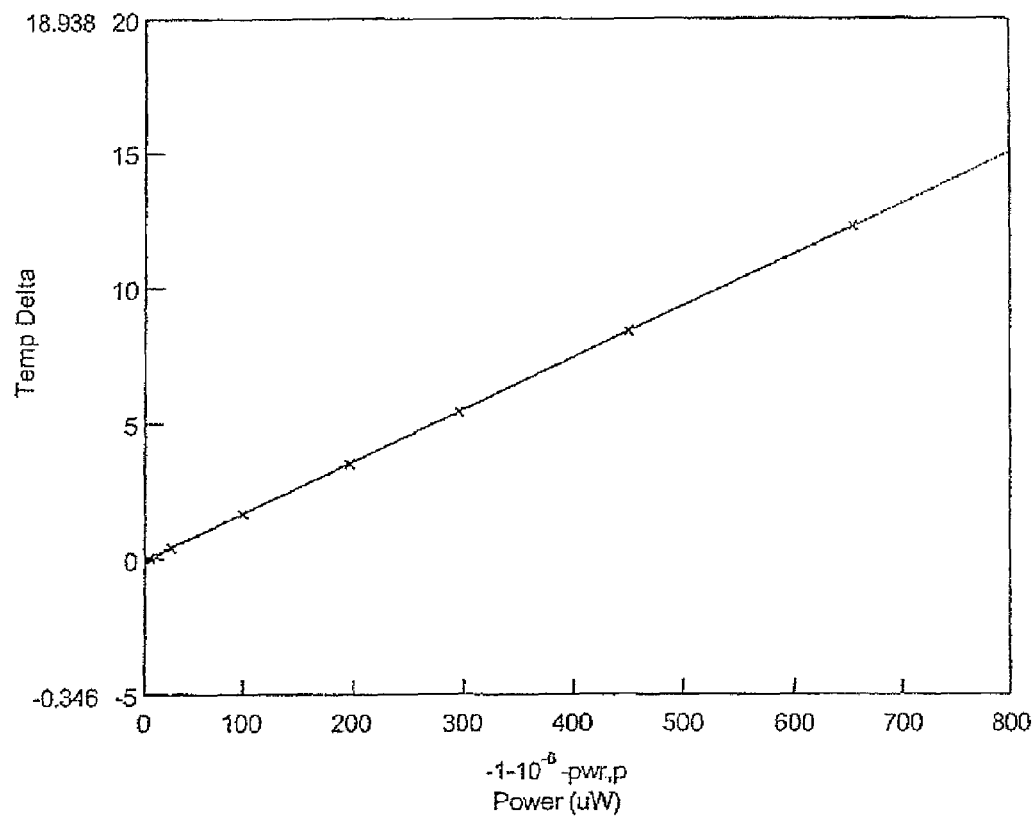
FIG. 2 is a graph of temperature change versus power for a device.

Referring to FIG. 2, a change in temperature versus power of a self-heating semiconductor device is shown. The graph of FIG. 2 is an example of the graphs generated for each measurement and heating device pair at various distances. Thus, the measurement with heating devices for FIG. 2 is illustrative examples, and should not be considered a limiting feature. Other examples are contemplated and can be easily determined by those of skill in the art in view of the present invention.

This illustrative information of FIG. 2 is the final result after extrapolation and all measurements and calculating steps resulting from the flow of the invention as described in more detail with reference to FIGS. 9 and 10. In the graph, the y-axis represents the change in temperature in degrees centigrade, and the x-axis represents the power applied to the device in micro Watts (μW) at 25° C. ambient temperature. The line on the graph was derived for heating bias conditions of $V_{gs}=V_{ds}=0V$ to 1V in 0.1V increments. These slopes were converted to temperature changes and plotted versus the applied power.

Figure 3:
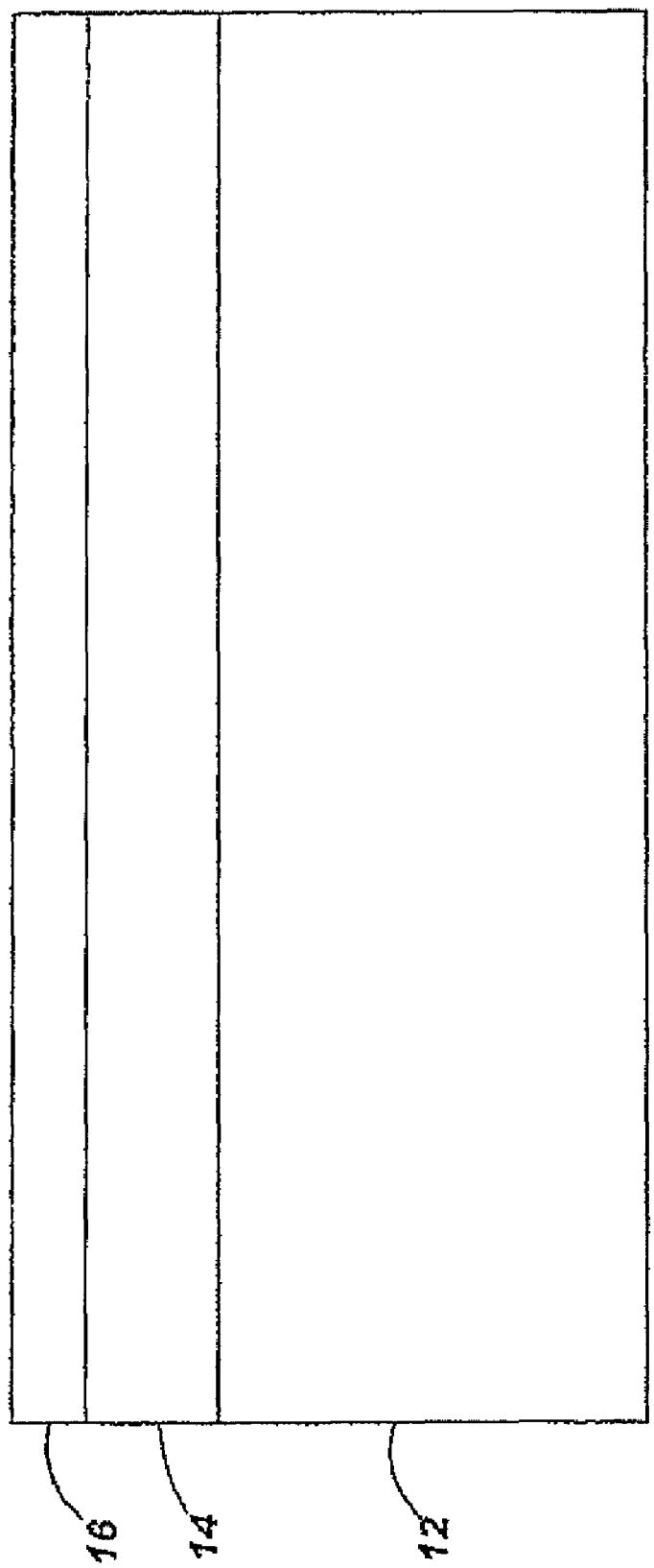
FIGS. 3-7 illustrates steps in manufacturing an embodiment of the invention.

FIGS. 3 through 7 illustrate steps in fabricating an embodiment of the self-heating monitor. Referring to FIG. 3, an SOI wafer is shown. The SOI wafer includes a silicon substrate 12 overlaid by a thin, buried oxide layer 14. On top of the buried oxide layer 14 is arranged a layer of silicon 16. The buried oxide layer 14 and silicon layer 16 may be formed on a silicon substrate 12 by any of the methods well-known in the art, such as, for example, a high-energy oxygen implant and then activating the oxygen to form the buried oxide layer 14.

Figure 4:
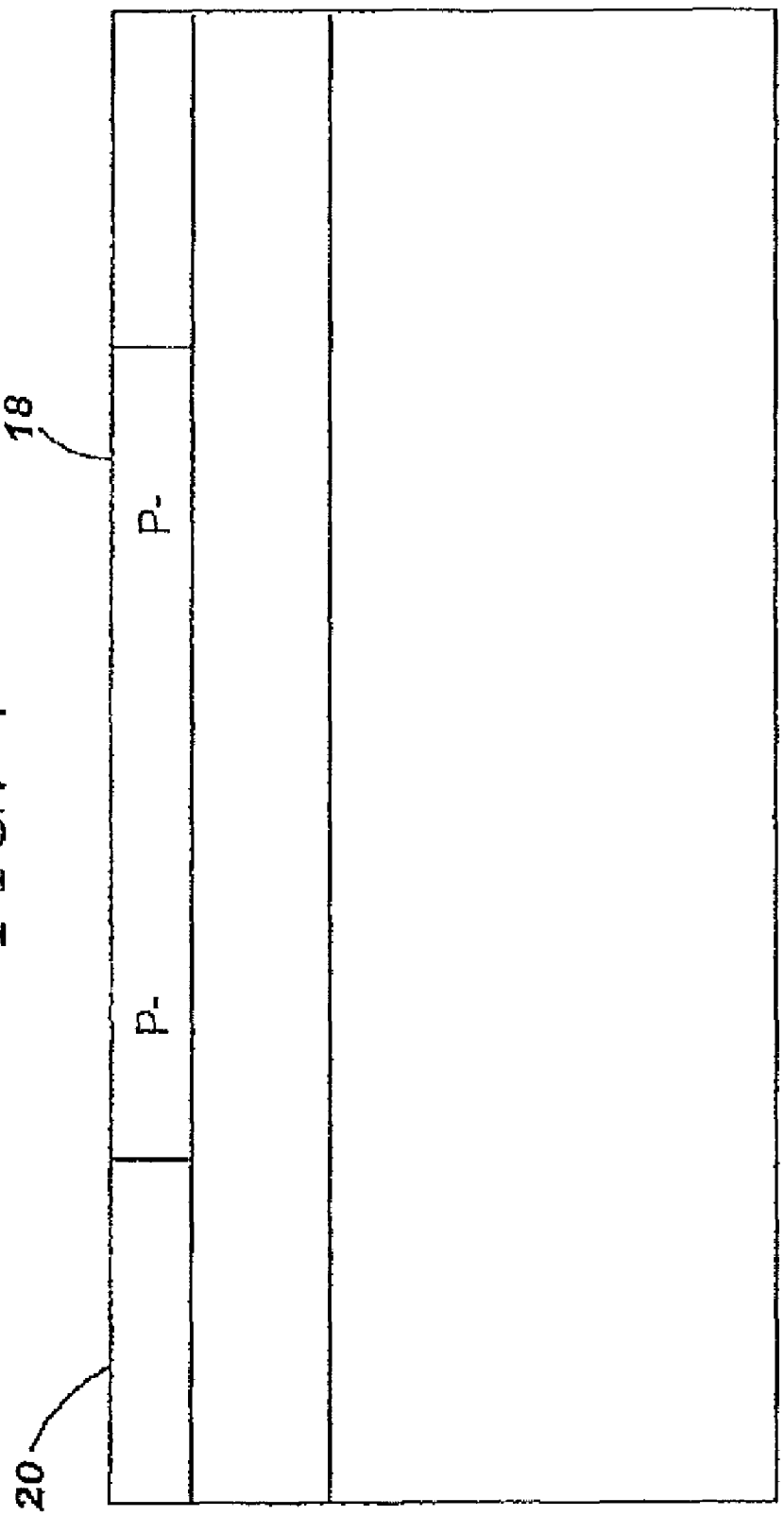

Referring to FIG. 4, well-known standard photo lithographic imaging and etching techniques are preformed to remove portions of the silicon layer 14 to form a silicon island 18 on top of the buried oxide layer 14. Next, shallow trench isolation oxides 20 are formed surrounding the edges of the silicon island 18. The oxide is deposited into the regions surrounding the edge of the silicon island 18 by any of the oxide deposition techniques well-known in the art. The silicon island 18 is then implanted with a well doping ion (P-type for N-channel devices, and n-type for P-channel devices) using any of the doping techniques well known in the art. In the example shown in FIG. 4, the channel regions of the two devices being fabricated are doped with P-type dopant.

Figure 5:
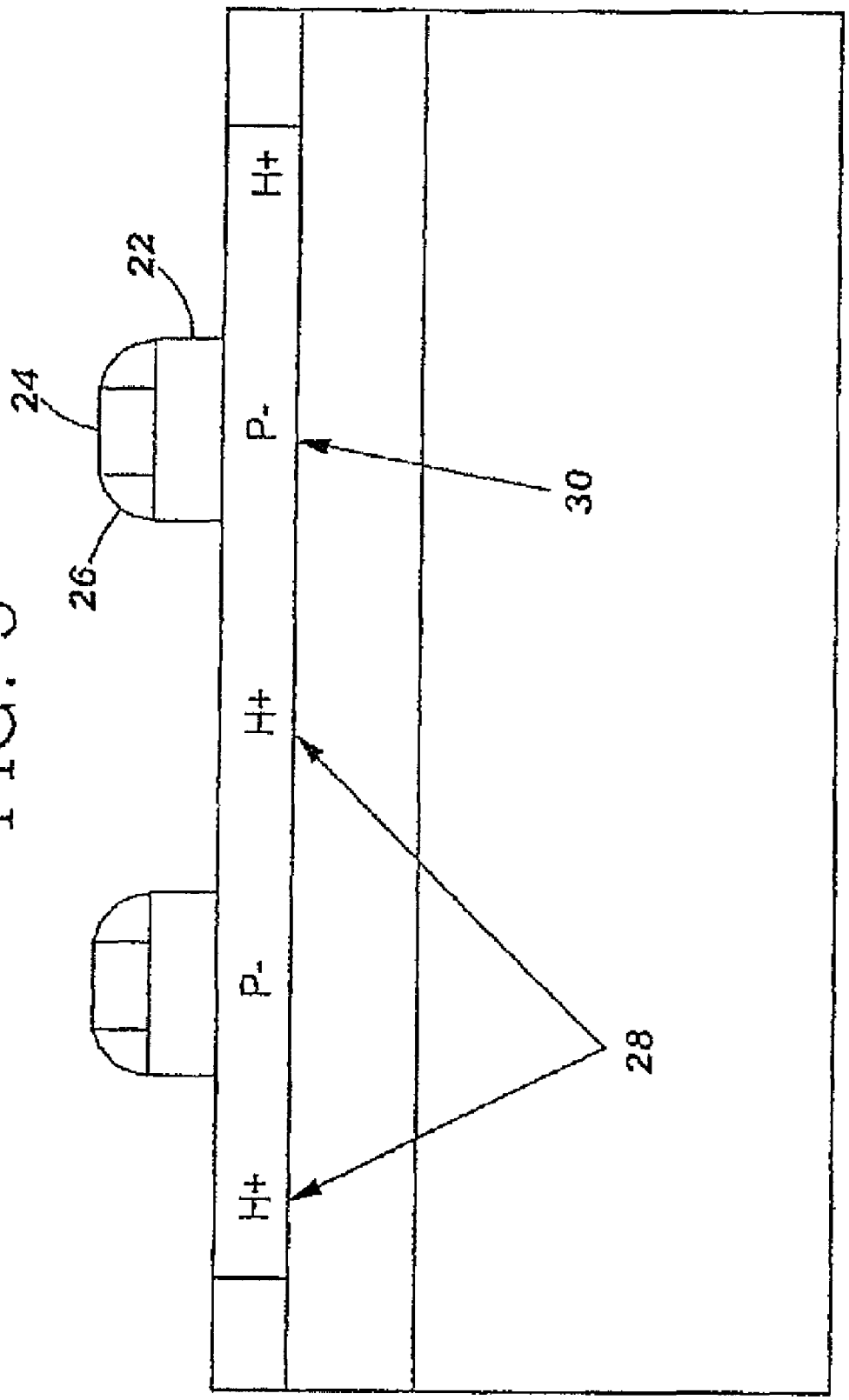

Referring to FIG. 5, the surface of the silicon island 18 is cleaned and a gate oxide 22 is formed on the surface of the island 18. The gate oxide 22 can be formed by any of the methods for depositing, imaging and etching gate oxides well known in the art. A gate polysilicon layer 24 is formed on top of the gate oxide 22, and patterned and etched to form the device gate structure using any of the methods well known in the art to fabricate gate polysilicon layers. After the gate polysilicon 24 is formed, spacers 26 are formed on top of the gate oxides 22 and abutting the edges of the gate polysilicon 24. The spacers 26 can be formed from materials and using methods well known in the art and include, for example, nitride or oxide spacers.

After the spacers 26 are formed, the region of the silicon island 18 not covered by the gate structures is implanted 19 with the appropriate dopant relative to the channel dopant. In this example, the channels are doped with p-type ions, and thus the regions in the silicon island 18 to either side of the gate structures is doped with n-type ions, as well as doping the gate polysilicon 24. Doping techniques which may be used for this step are well known in the art. In this example, the n-doped regions form the source and drain regions 28, and the p-doped region forms the channel 30 of the measurement and heating device pair The dopant types, concentrations and energy levels would be those appropriate for whichever type of device is being fabricated, and are well-known in the art.

Figure 6:
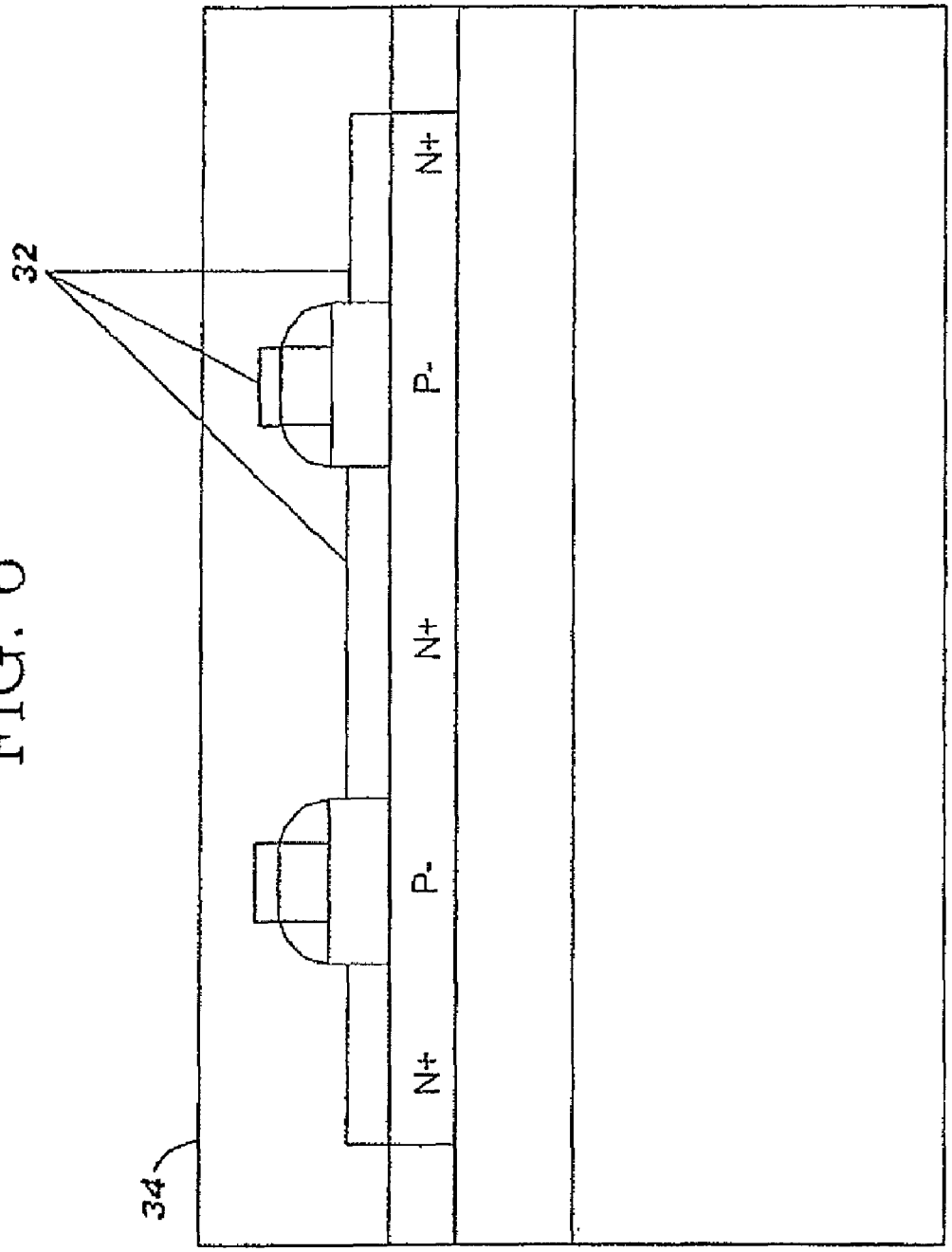

Referring to FIG. 6, the silicide layer 32 is formed over the source and drain regions, 28, and the gate-polysilicon 24. After the silicide layer 32 is formed, a planar oxide layer 34 is deposited over the shallow trench oxide regions 20, silicide 32 and gate structures. The planar oxide 34 can be deposited using any of the methods well-known in the art.

Figure 7:
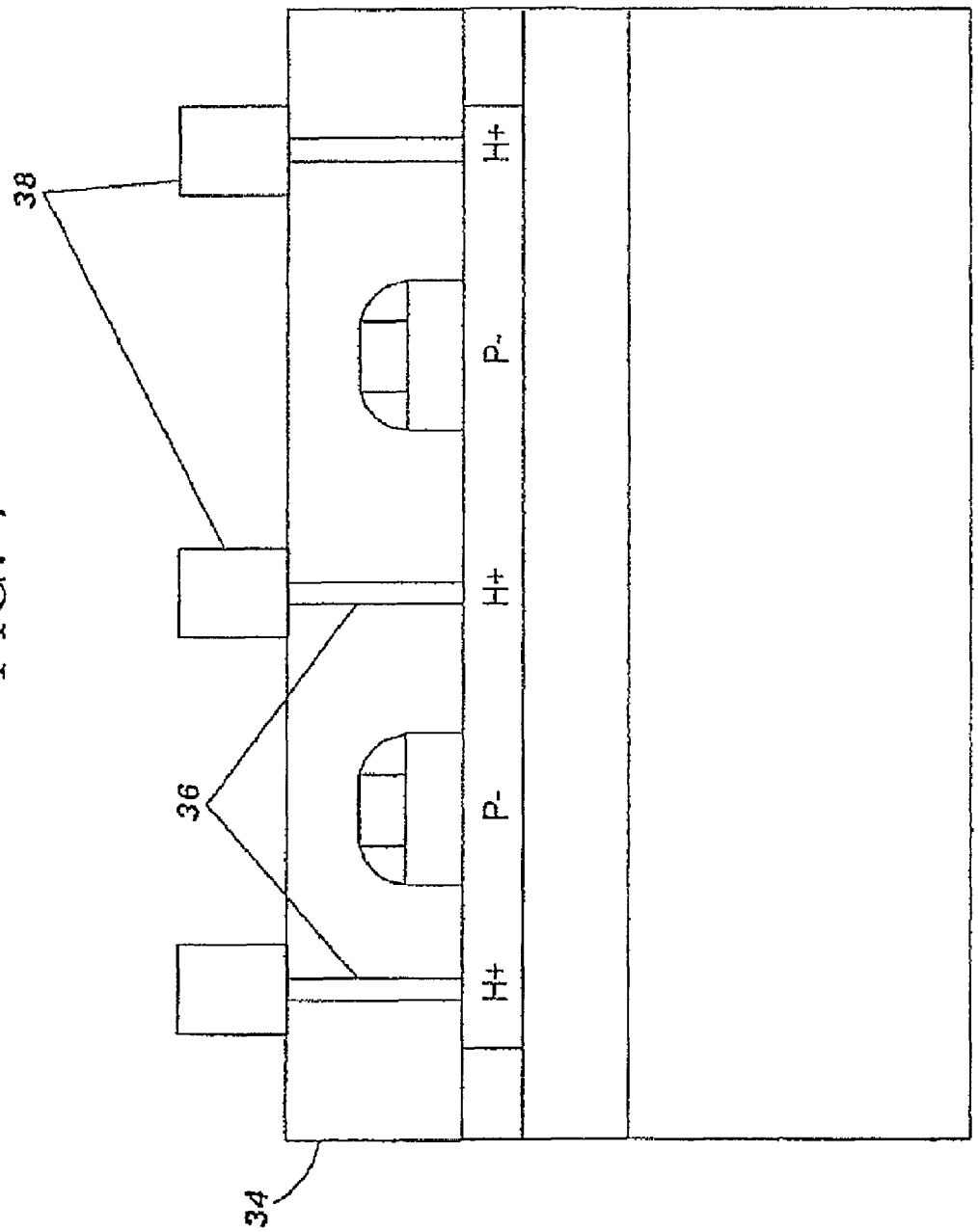

Referring to FIG. 7, vias 35 are patterned and etched in the planar oxide 34 from a top surface of the planar oxide 34 down to the silicon island 18. The vias 35 are filled with conductive material, such as metal to form contacts 36 to the source and drain regions 28 of the silicon island 18. After the contacts 36 are formed, a first metal wiring layer 38 is deposited on top of the planar oxide 34. The first metal wiring layer is then etched to form metal contacts 38 on a top surface of the planar oxide 34, in electrical contact with the contacts 36.

Figure 8:
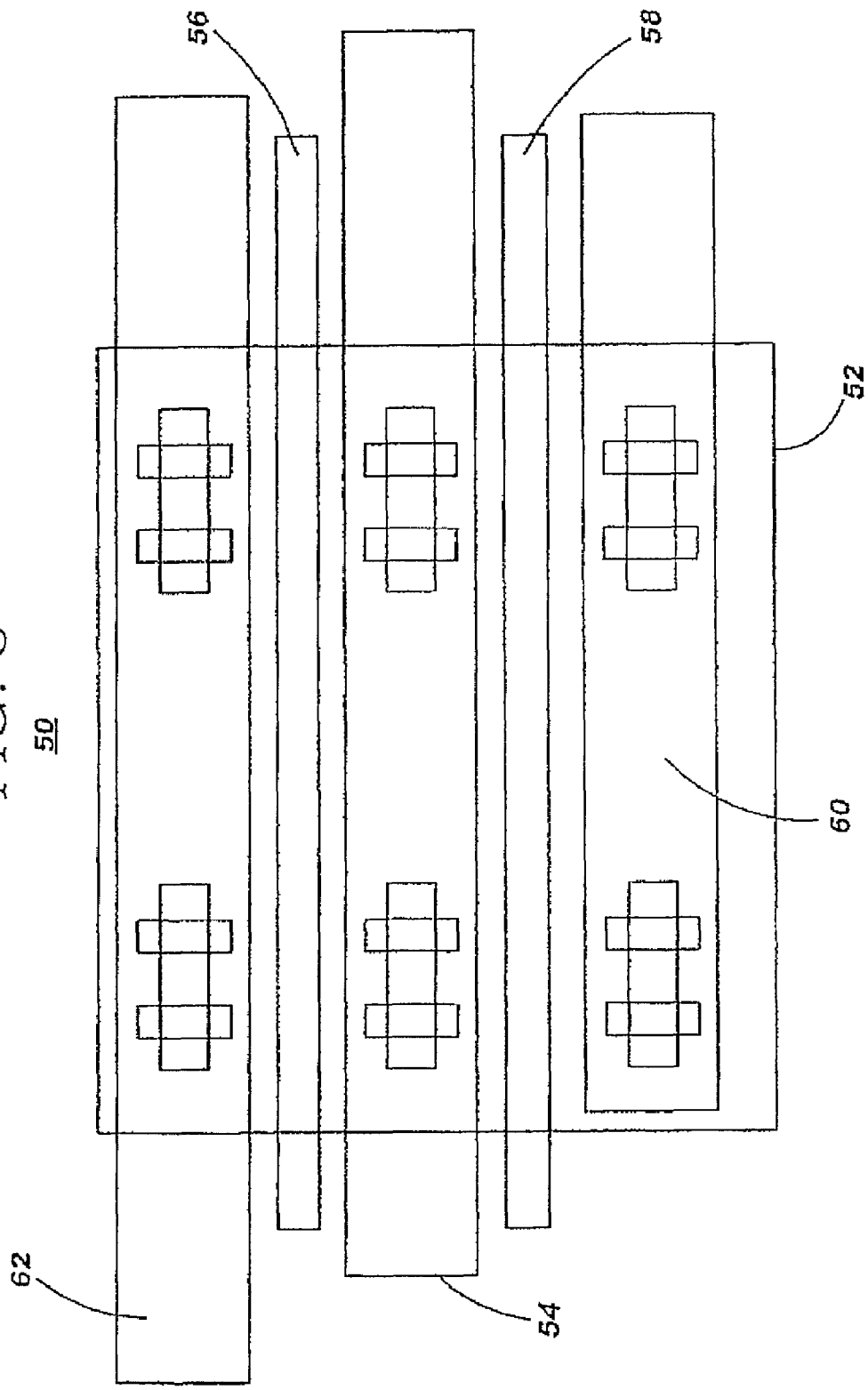
FIG. 8 illustrates a top view of a surface of an embodiment of the device in accordance with the invention.

Referring to FIG. 8, a top view of an embodiment of the device 50 is shown, illustrating various metal contacts to the devices on silicon island 52. The silicon island 52 has a heating device drain metal contact 60, and a measurement device drain contact 62. Also included on the silicon island 52 is a common source contact 54 which leads to the source of both the underlying measurement device and the heating devices. A measurement gate contact 56 and a heating gate 58 are also included on the silicon island 52.

It should be noted that although a particular example of forming the heating and measuring devices is discussed above, any fabrication process which produces a pair of semiconductor devices such as FETs in thermal communication with one another may be suitable for the temperature measurement. As such, the temperature measurement method can work with any pair of devices where one of the devices produces heat, and the other device responds to that heat in some measurable way, such as one of its electrical characteristics changing in accordance with its temperature. It should also be noted that while the examples discussed above use two devices of similar design for heating and measuring, the measurement device and the heating device may be of completely different designs as long as the heating device is capable of heating and the measurement device is capable of measuring temperature and the two are in thermal contact. Additionally, two devices may be in thermal contact with one another without actually being in physical contact with one another. Thus, two devices may be in thermal contact while actually touching one another, and two devices may be in thermal contact where the thermal contact is through an intermediate thermal conductor such as a length of silicon in physical contact with one another.

It should be noted that the silicon island may have a perimeter which describes a square as well as other geometric shapes such as rectangles, circles, oblongs, triangle, etc. Additionally, although the measurement device in FIGS. 3-7 show two FETs, the measurement device can be made with more FETs.

In general, the measurement method relies upon two semiconductor devices where one device functions as a heat source, and the other devices functions as a temperature measurement. For example, the temperature measurement method may rely on two FETs fabricated on a single silicon island, which is substantially surrounded on all sides by material having low thermal conductivity as discussed below. One of the FETs is referred to as the heating device, and generates heat when it is powered up. The second device is referred to as the measurement device, and measures the temperature in its active region by sensing a change in a prescribed electrical characteristic of its active region, which is then correlated to temperature. In implementation, the distance between the heating device and the measurement device is varied and thus the temperature at the heating device may be extrapolated from multiple measurements.

To determine the correspondence between power applied to the heating device and its temperature, a series of measurements for each heating/measurement pair is performed where varying amounts of power are applied to the heating device and the temperature at the measurement device is determined. This process may be repeated for the multiple pairs of heating/measurement devices where each pair has a different distance between the heating and measurement device. By measuring the temperature at varying distances from the heating device, the data can be extrapolated and the temperature of the active region of the heating device under various amounts of power can be determined. Typical distances between the heating device and the measurement device range from ¼ of a micron to one or two microns. It should be realized that due to the thermal characteristics of the silicon island, multiple measurements using different pairs of heating and measurement devices in different geometries may be required to accurately determine the relationship between power applied to the heating device and its temperature. For example, multiple pairs of heating and measurement devices may be made where each measurement device corresponds to a particular heating device and with a different separation distance.

Before actual measurements can be made, the measurement device of each heating/measurement pair should be calibrated. The calibration of the measurement device is performed by measuring a particular electrical characteristic of the active region of the measurement device with the measurement device held at a known ambient temperature. For example, the measurement device can be held at 25° C. and the sub-threshold voltage slope is measured in a range from 0-0.4 volts driving voltage of the heating device. The sub-threshold voltage slope may be measured by holding the gate voltage at 0 and sweeping the drain through the desired voltage range. Next, 0.1V is applied to the drain of the heating device and another sweep of the drain of the measurement device is done. This process maybe repeated in 0.1 V steps of the drain of the heating device until the entire desired range is swept through. Other voltage steps are also contemplated.

The collected data produces a sub-threshold voltage slope at each different increment of power corresponding to the voltage applied to the drain of the heating device as illustrated by the example of FIG. 1. Additionally, the current of the heating device is measured so that the power being dissipated by the device is known. Such a process is repeated for multiple temperatures and a sub-threshold voltage slope versus temperature relationship is derived. For example, the process is repeated for 15° C., 75° C. and 100° C. temperature points. Accordingly, four sub-threshold voltage slopes as a function of ambient temperature are determined with no self-heating at the heating device to calibrate the measurement device.

For the typical geometry of heating/measurement device, there may be thermal effects which would not be present during operation of the heating device in an actual application as distinguished from having its temperature measured. For example, the presence of a measurement device may require metal contacts which otherwise would not normally be there. Such metal contacts may act as heat sinks which conduct heat away from the heating device, thereby effectively reducing the temperature below that at which it would normally operate. This thermal effect can be understood and accounted for by fabricating the heating/measurement device pairs so that such thermal effects are the same from pair to pair. Accordingly, it is advantageous to make the thermal resistance between the devices for each pair of devices as similar as possible.

Figure 9:
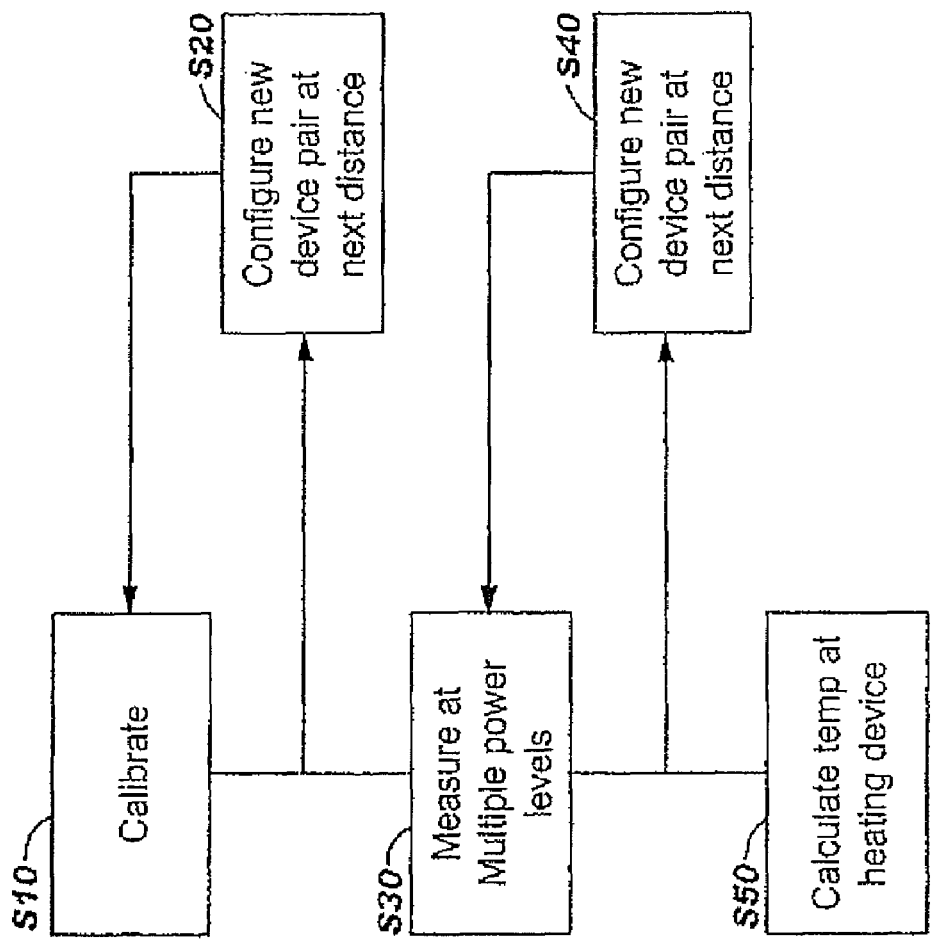
FIG. 9 illustrates a flow-chart of an embodiment of the measurement process in accordance with the invention.

Referring to FIG. 9, a flow chart of an embodiment of the measurement method is shown. FIGS. 9 and 10 may equally represent a high-level block diagram of components of the invention implementing the steps thereof. Several of the steps of FIGS. 9 and 10 may be implemented on computer program code in combination with the appropriate hardware. This computer program code may be stored on storage media such as a diskette, hard disk, CD-ROM, DVD-ROM or tape, as well as a memory storage device or collection of memory storage devices such as read-only memory (ROM) or random access memory (RAM). Additionally, the computer program code can be transferred to a workstation over the Internet or some other type of network.

In step S10, a sensing device of a device pair having a sensing device and a heating device is calibrated. The calibration may include of determining the variation of a particular electrical characteristic of the sensing device as a function of temperature. In step S 20, the calibration process S10 is repeated for a different distance between the sensing and heating device. This typically involves a different device pair arranged at a distance different from the previously calibrated device pair.

In S30 of FIG. 9, a temperature measurement is processed for a device pair at a particular distance. The temperature measurement typically involves running the heating device at various power levels. In S40, the temperature measurement is performed at a different distance for a device pair, and typically involves a different device pair arranged at a distance different from the previously measured device pair. S50 includes calculating a temperature versus power level relationship for the heating device using the data collected at different power levels and different distances between the sensing and heating devices.

Figure 10:
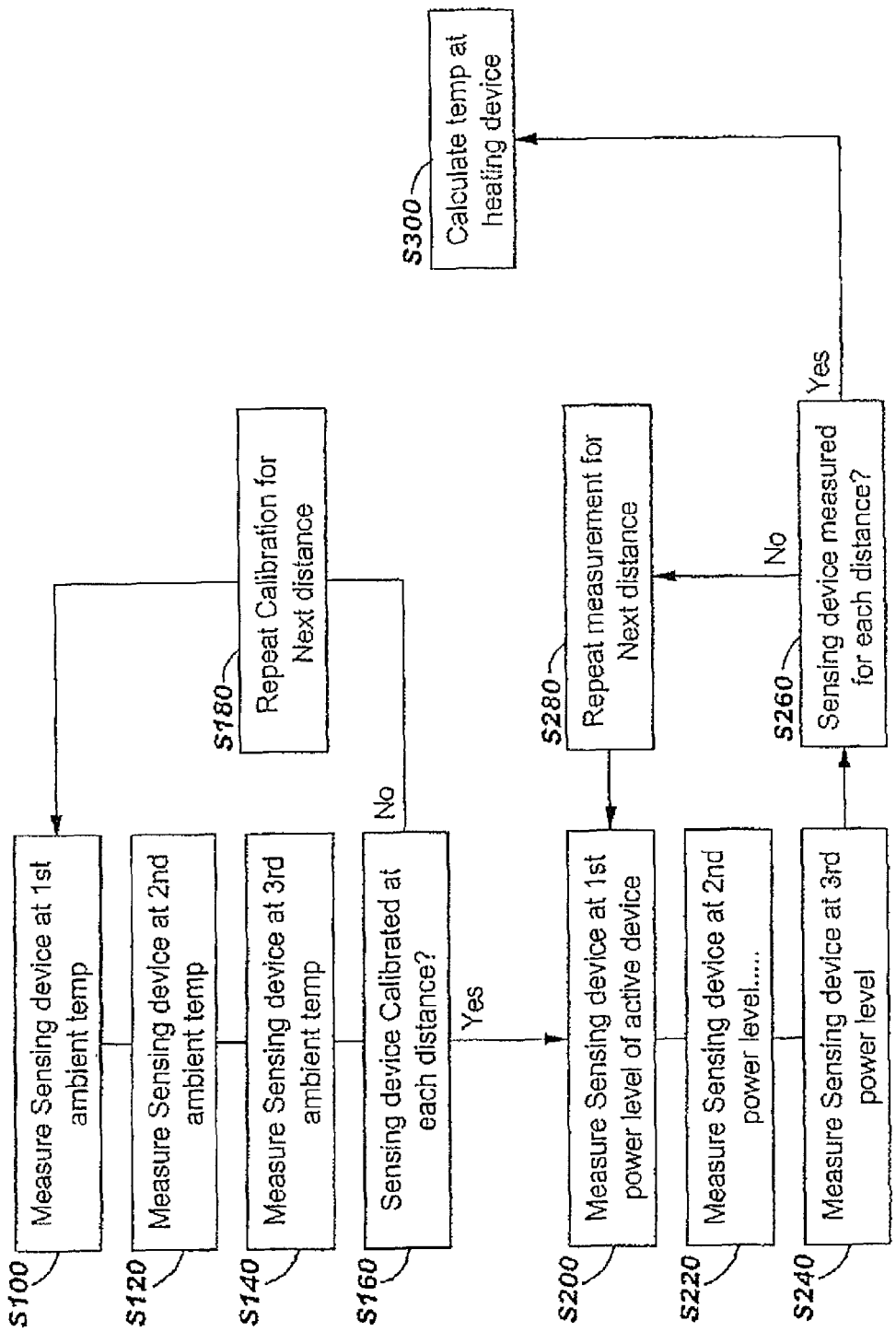
FIG. 10 illustrates a flow-chart of an embodiment of the measurement process in accordance with the invention.

Referring to FIG. 10, an example of an embodiment of the measurement method is shown. In S100, a sensing device of a first device pair having a sensing and a heating device is calibrated for a chosen separation distance. The calibration process includes monitoring a particular electrical characteristic of the sensing device while the device pair is held at a selected ambient temperature with no power being applied to the heating device. For example the sub-threshold voltage slope of the sensing device may be monitored while the device pair is held at 25° C. In S120, the calibration process is repeated while the device pair is held at a second ambient temperature, such as, for example, 50° C. In S140, the calibration process is repeated at a third temperature, such as, for example 100° C. A relationship between the temperature of the device and the chosen electrical characteristic is then calculated by fitting the data to a curve, such as by a least squares method. Alternatively, the data may be fitted to a curve using any of the curve fitting software packages which are well known in the art In S160, the calibration process is checked to determine whether the process had been performed for each selected distance. If device pairs are to be calibrated at other distances, the calibration process is repeated at S180 for all the chosen temperatures at a different distance between a sensing and heating device. This typically involves a new device pair having of a similar sensing and heating device as in the previous device pair, but arranged with a different separation distance.

After the calibration steps, S100, S120, S140, S160 and S180 are complete, a measurement is made in S200 at a first power level for the heating device and a first distance separating the device pair. The measurement is repeated for a second and third power level in steps S220 and S240, respectively. When all the predetermined power levels have been measured, the process is repeated in S260 and S280 if other distances are to be measured.

Once all measurement data has been collected in steps S200, S220, S240, S260 and S280, a relationship between temperature and power of the heating device is calculated using, for example, any of the commercially available curve fitting software packages capable of fitting data to a curve. The relationship between the temperature and power of the heating device is typically an exponential relationship, although other relationships are possible and can be accommodated by the method.

Table 1 shows examples of dimensions of various devices which were fabricated for measurements of temperature using the above-described method. As can be seen from Table 1, silicon islands of various lengths and widths were used as well as gate spacings between the gates of the heating and measurement device. The devices also had various numbers of contacts, ranging from 2 to 4 to 6. Additionally, the comments section includes information about the device geometry such as gate spacing and length.

TABLE 1

| Device | Ld (μm) | Wd (μm) | Gate Spacing (μm) | Rx Length (μm) | Contacts | Comments |
|---|---|---|---|---|---|---|
| M1S1 | 0.875 | .1225 | 0.2625 | 0.8925 | 2/3X | Very narrow Rx |
| M1S2 | 0.875 | 1.75 | 0.98 | 1.61 | 4/4X | Wide space between gates without Al bridge |
| M1S3 | 0.875 | 1.75 | 0.5075 | 1.1375 | 4/4X | Medium space between gates with Al bridge |
| M1S4 | 0.875 | 1.75 | 0.2625 | 0.8925 | 4/3X | Base device |
| M2S1 | 0.875 | 0.875 | 0.2625 | 0.8925 | 2/3X | Narrow Rx |
| M2S3 | 0.875 | 1.75 | 0.2625 | 0.8925 | 6/3X | Extra contacts & cooling fins |
| M2S4 | 0.875 | 1.75 | 0.2625 | 35.9351 | 4/3X | Very long Rx |
| M3S1 | 0.875 | 1.75 | 0.2625 | 2.6425 | 4/3X | Medium long Rx |

The various device geometries are labeled, for example, M1S1. Thus, various device geometries were tested.

Table 2 shows the heating effects for three different gate spacings of 0.26 micron, 0.51 micron and 0.98 micron. The column labeled Waf T5TY and at Waf Q878 each represent different SOI wafers from which the respective measurement devices were manufactured. For example, the device type M1S4 was manufactured on two different wafers, the first labeled T5TY, and the second labeled Q878.

TABLE 2

| PC spacing | Waf T5TY Deg C./mW/u | Waf Q878 Deg C./mW/u | Comments |
|---|---|---|---|
| Base device, PC-PC = 0.26 | 33.25 | 36.75 | M1S4-4CA/3X |
| PC-PC = 0.51 | 18.8 | 19.1 | M1S3-4CA/4X, Al bridge |
| PC-PC = 0.98 | 5.5 | 7.9 | M1S2-4CA/4X, No Al bridge |

Referring to Table 3, the results of adding contacts is shown to the device M1S4 and the device M2S3.

TABLE 3

| Added CA | Waf T5TY Deg C./mW/u | Waf Q878 Deg C./mW/u | Comments |
|---|---|---|---|
| Base device, 4CA/3X | 33.25 | 36.75 | M1S4 |
| 6CA/3X & "cooling fins" | 26.25 | 31.5 | M2S3 |

Referring to Table 4, devices of different widths are shown and the results thereto.

TABLE 4

| Device widths/Ca/u | Waf T5TY Deg C./mW/u | Waf Q878 Deg C./mW/u | Comments |
|---|---|---|---|
| Base device, 4CA/3X, W = 1.75 | 33.25 | 36.75 | M1S4 |
| 2CA/3X, W = 0.825 | 28.5 | 30.3 | M2S1 |
| 2CA/3X, W = 0.1225 | 3.1 | 0.8 | M1S1 |

Referring to Table 5, the results of various RX paths of the device are shown for the devices M1S4, M3S1 and M2S4.

TABLE 5

| RX past device | Waf T5TY Deg C./mW/u | Waf Q878 Deg C./mW/u | Comments |
|---|---|---|---|
| Base device, RX = 0.89 | 33.25 | 36.75 | M1S4 |
| RX = 2.64 | 33.25 | 26.3 | M3S1 |
| RX = 35.9 | 30.9 | N/A | M2S4 |

In the embodiments described above, the heat reducing effects of the contacts between the gates was considered negligible. However, to more accurately determine the self heating, the embodiments of FIGS. 11-13 take into account the thermal resistance of the contacts in order to more accurately assess the self heating. As should be understood, the contacts create a thermal resistance. That is, the contacts act as heat sinks which take heat away from the silicon island 52 which, in turn, reduces the temperature at the measurement gate contact 56. Accordingly, without taking into account the number of contacts, the reading of the temperature may vary by a certain offset, equal with a proportionality to the number of contacts.

Figure 11:
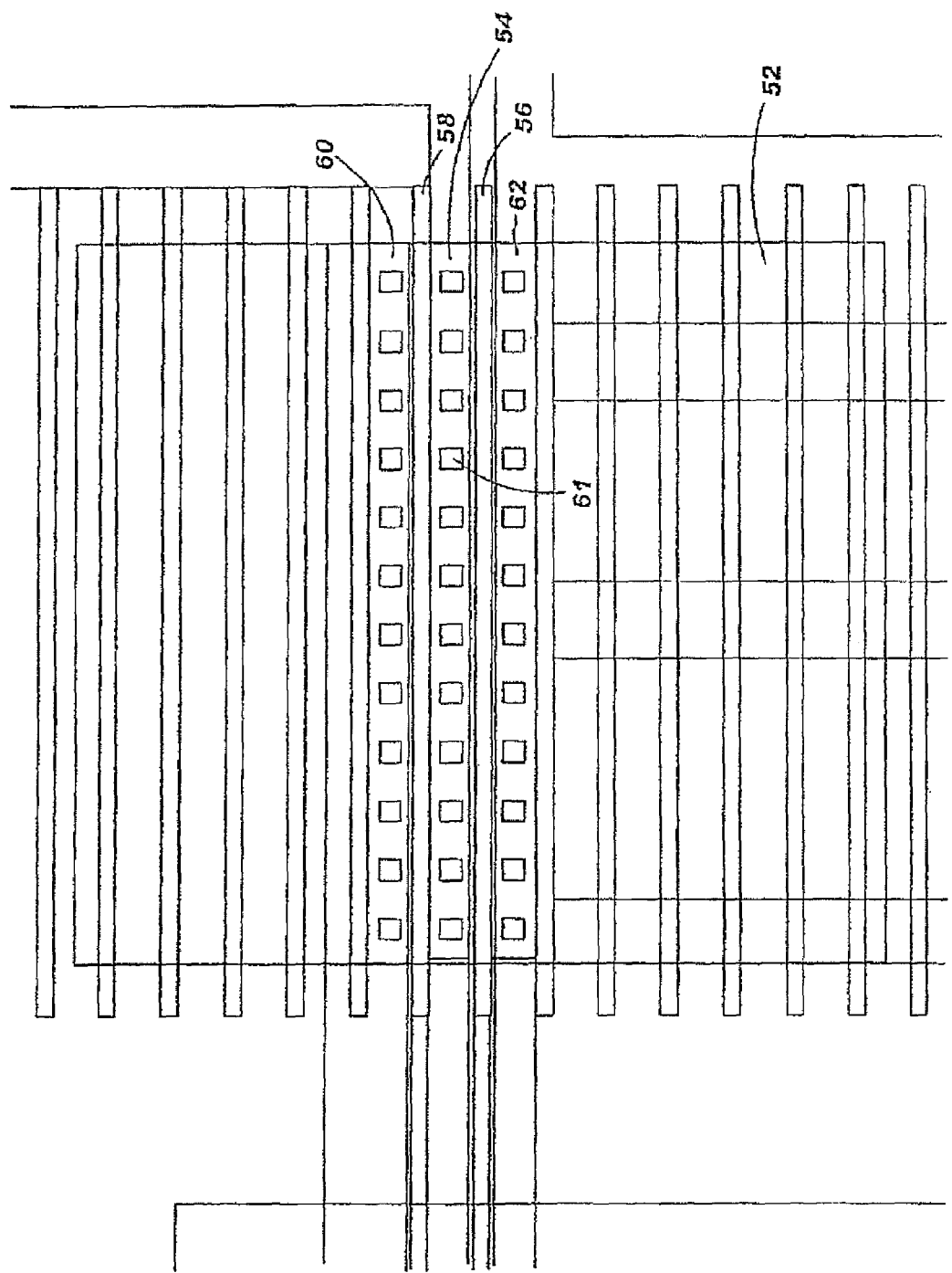
FIGS. 11-12 are illustrative embodiments of wide devices with varying contact amounts in accordance with the invention.
Figure 12:
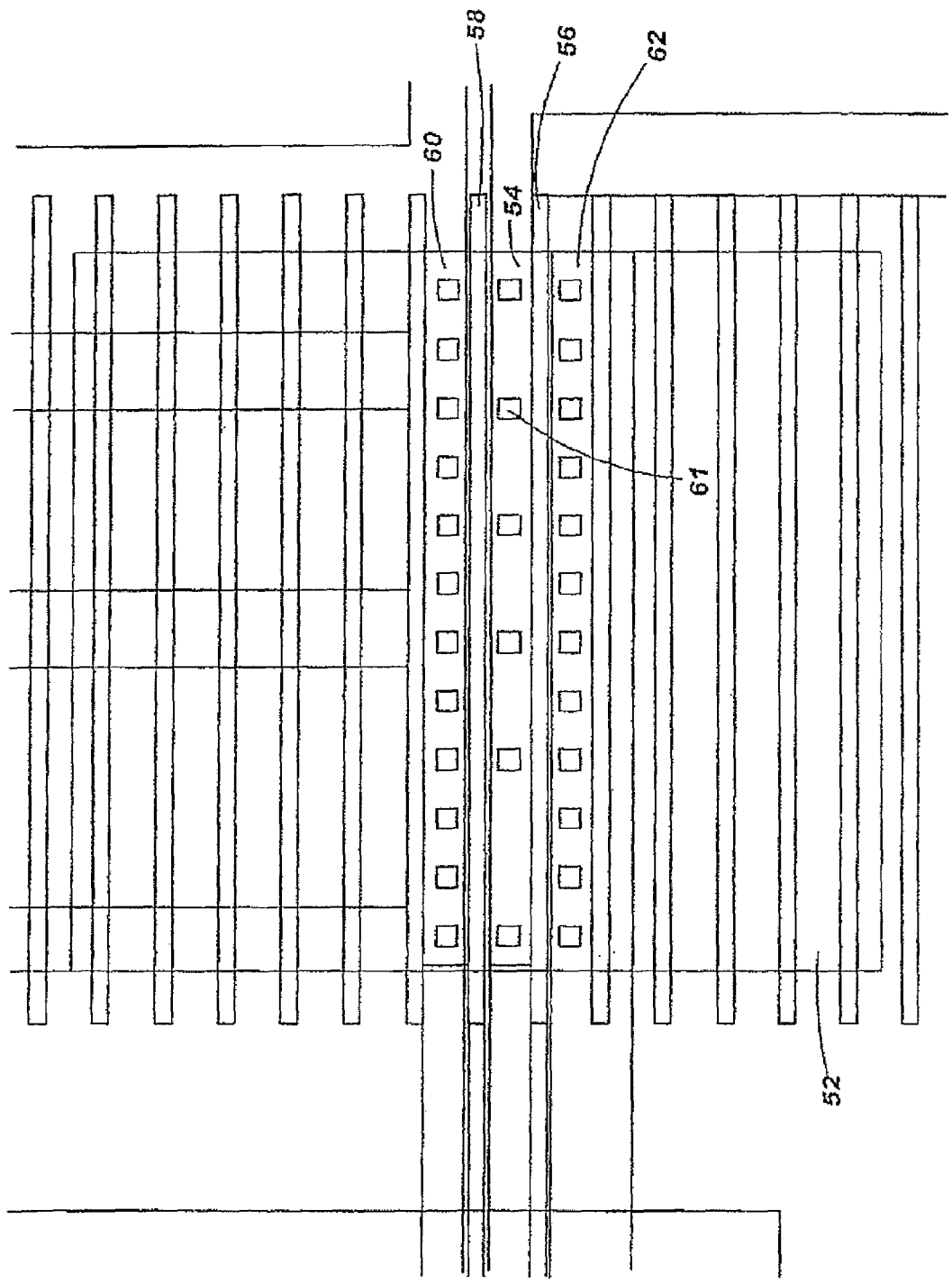
Figure 13:
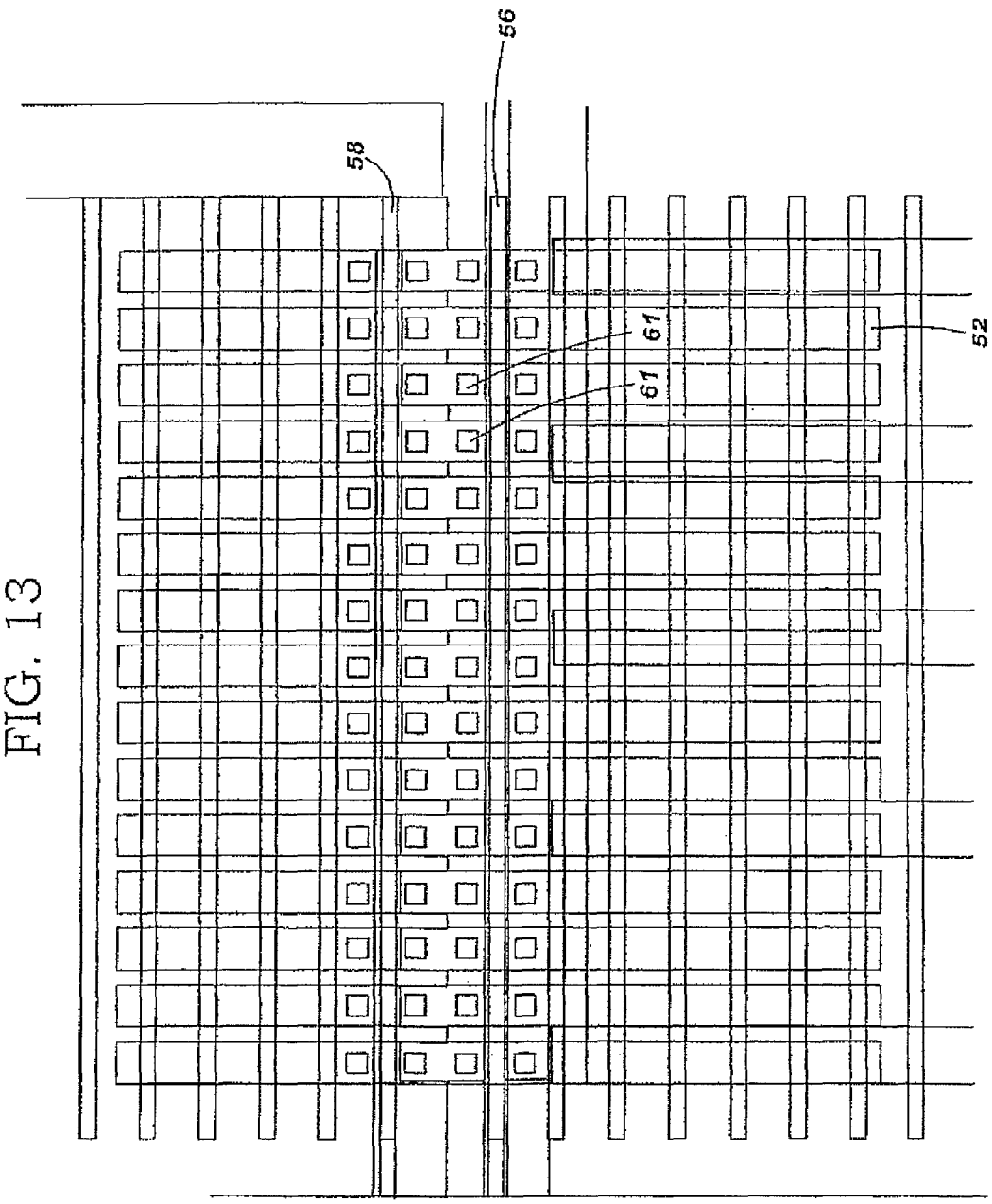
FIG. 13 is an illustrative embodiment of narrow device with varying contact amounts in accordance with the invention.

But, to compensate for this offset, the technique of FIGS. 11-13 use a measurement differential taken with at least two devices having a different number of contacts and extrapolating the results to zero contacts. In embodiments, this is accomplished by adding or subtracting the number of contacts between two or more different devices, as discussed below.

The measuring technique associated with FIGS. 11-13 is applicable to both wide and narrow type devices, known in the art. In the measuring technique of this aspect of the invention, the number of contacts will vary on the diffusion between the measurement gate contacts 56 and heating gate contacts 58 of different measured devices to establish the rate of temperature change per contact. Once the rate of temperature change is established for the devices, it is then possible to extrapolate that change to zero contacts to determine the actual device temperature without the effect of the offsetting contacts between the gates.

By way of example, FIGS. 11 and 12 represent a top view of a wide device 50. Similar to the previous embodiments, in FIGS. 11 and 12, the silicon island 52 has a heating device drain metal contact 60 and a measurement device drain contact 62. Also provided on the silicon island 52 is a common source drain contact 54 which leads to the source drain of both the underlying measurement device and the heating device. A measurement gate source contact 56 and a heating gate source 58 are further provided on the silicon island 52. FIG. 11 shows 12 contacts on the common drain 61; whereas, FIG. 12 shows six contacts. The different number of contacts between FIGS. 11 and 12 provides for a measured temperature differential in accordance with this aspect of the invention.

It should be understood that any number of contacts may be used with the extrapolative method of this embodiment by either adding or subtracting contacts. By illustrative example, in the embodiment of a wide device such as shown in FIGS. 11 and 12, it is preferable to subtract contacts. Thus, FIG. 11 includes 12 contacts and FIG. 12 shows six contacts. However, in narrow devices such as shown in FIG. 13, it is preferable to add contacts. Thus, in the narrow device example, it may be necessary to add an additional contact $61_A$ to reduce the thermal resistance which, in turn, results in a measured heat differential (e.g., difference of the thermal load) between a first narrow device with one contact and a second narrow device with two contacts. Once these temperature differentials are measured, the results are then extrapolated to zero contacts, in any well known extrapolative technique.

In one aspect of the invention, for a wide device the procedure should be applied to the smallest gate spacing, since the measurement temperatures (signal) is highest and the effect will be largest. The number of contacts is then reduced to allow the slope of the measured temperature to be determined versus the number of contacts. To help calibrate the narrow device the total number of contacts is kept the same as a case where all the contacts are an equal distance from the gate edge to help further quantify the results for one case. Additional cases with fewer contacts could also be added to further determine the proper scaling.

While the invention has been described in terms of embodiments, those skilled in the art will recognize that the invention can be practiced with modification within the spirit and scope of the appended claims. For example, the invention can be readily applicable to multiple measurement devices associated with the single heating device.

What is claimed is:

1. A computer program product comprising a non-transitory computer readable storage medium having readable program code embodied in the medium, the computer program product includes at least one component operable to:
   measure a change in at least one electrical characteristic of a first sensing device caused by heat generated at a first heating device;
   calculate a temperature of the first heating device using the measured change in the at least one electrical characteristic;
   determine an offset between the first heating device and at least a second heating device, each having a different number of contacts; and
   extrapolate the offset to zero contacts.

2. The computer program product of claim 1, wherein the first heating device and the first sensing device are arranged on the SiGe island.

3. The computer program product of claim 1, wherein the first sensing device, the first heating device, and a common source contact arranged on a SiGe island constitute an apparatus, and the common source contact leads to a source of both the first heating device and the first sensing device.

4. The computer program product of claim 1, wherein the calculating is based on a temperature versus power level relationship for the first heating device using the measured change in the at least one electrical characteristic of the of the first sensing device at different power levels and different distances from the first heating device.

5. The computer program product of claim 1, wherein the at least one electrical characteristic is a sub-threshold voltage slope.

6. The computer program product of claim 1, wherein the measuring includes measuring a series of measurements between the first sensing device and the first heating device at varying amounts of power applied to the first heating device.

7. The computer program product of claim 1, wherein the measuring includes measuring a series of measurements between the first sensing device and the first heating device at varying distances.

8. The computer program product of claim 1, wherein the first heating device and the first sensing device are a field effect transistor.

9. The computer program product of claim 1, wherein the at least one electrical characteristic comprises drain current versus gate bias voltage.

10. The computer program product of claim 1, wherein the at least one electrical characteristic comprises sub-threshold voltage slope swing.

11. The computer program product of claim 1, wherein the at least one component is further operable to calibrate the first sensing device by measuring a particular electrical characteristic of an active region of the first sensing device held at a known ambient temperature.

12. The computer program product of claim 1, wherein:
   the measuring includes:
      measuring the change in the at least one electrical characteristic of the first sensing device caused by the heat generated at the first heating device with a first number of contacts;
      measuring the change in the at least one electrical characteristic of the first sensing device caused by the heat generated at the first heating device with a second number of contacts; and
   the calculating includes:
      calculating the temperature of the first heating device with the first number of contacts and the second number of contacts using the measured change in the at least one electrical characteristic; and
      extrapolating results of the measurement obtained with the first number of contacts and the second number of contacts to the zero contacts.

13. The computer program product of claim 1, wherein the measuring includes establishing an amount of temperature change per contact between the first heating device and the second heating device having the different number of contacts and the calculating includes extrapolating results of the measurement step to the zero contacts to determine an actual device temperature without an offsetting effect of the contacts.

* * * * *